(12) United States Patent
Batta et al.

(10) Patent No.: US 7,605,148 B2
(45) Date of Patent: Oct. 20, 2009

(54) AQUEOUS ORAL SOLUTION OF BISPHOSPHONIC ACID

(75) Inventors: Ramesh Babu Batta, Hyderabad (IN); Umesh Nandkumar Khatavkar, Hyderabad (IN); Hidaytulla Shamshuddin Aga, Hyderabad (IN); Kishor Dattatray Deo, Hyderabad (IN); Sivakumaran Meenakshisunderam, Hyderabad (IN)

(73) Assignee: Aurobindo Pharma Ltd., Hyderabad, Andhra Pradesh (IN)

( * ) Notice: Subject to any disclaimer, the term of this patent is extended or adjusted under 35 U.S.C. 154(b) by 0 days.

(21) Appl. No.: 12/082,796

(22) Filed: Apr. 14, 2008

(65) Prior Publication Data

US 2009/0029946 A1    Jan. 29, 2009

(30) Foreign Application Priority Data

Apr. 16, 2007    (IN) .......................... 799/CHE/2007

(51) Int. Cl.
*A61K 31/66* (2006.01)
(52) U.S. Cl. ...................................................... 514/102
(58) Field of Classification Search .................. 514/102
See application file for complete search history.

(56) References Cited

U.S. PATENT DOCUMENTS

| | | | | |
|---|---|---|---|---|
| 5,843,924 | A * | 12/1998 | Brenner et al. ............... | 514/108 |
| 7,008,640 | B2 * | 3/2006 | Watanabe et al. ............ | 424/458 |
| 7,038,083 | B2 * | 5/2006 | Lidor-Hadas et al. ......... | 564/15 |
| 2004/0082545 | A1 * | 4/2004 | Handreck et al. ............. | 514/89 |

* cited by examiner

*Primary Examiner*—Raymond J Henley, III
(74) *Attorney, Agent, or Firm*—Jay R Akhave

(57) ABSTRACT

The present invention relates to stable aqueous oral formulation of bisphosphonic acid or its pharmaceutically acceptable salts. More particularly, the present invention relates to stable aqueous oral formulation of alendronate sodium. The present invention also relates to a process for the preparation of stable aqueous oral formulation of alendronate sodium.

10 Claims, No Drawings

AQUEOUS ORAL SOLUTION OF BISPHOSPHONIC ACID

CROSS REFERENCE TO THE RELATED APPLICATION

This application claims the priority of an Indian Patent application No. 799/CHE/2007 filed on Apr. 16, 2007.

FIELD OF THE INVENTION

The present invention relates to stable aqueous oral formulation of bisphosphonic acid or its pharmaceutically acceptable salts. More particularly, the present invention relates to stable aqueous oral formulation of alendronate sodium.

The present invention also relates to a process for the preparation of stable aqueous formulation of alendronate sodium.

BACKGROUND OF THE INVENTION

Alendronate sodium is chemically known as (4-amino-1-hydroxybutylidene) bisphosphonic acid monosodium salt. Alendronate as disclosed in U.S. Pat. No. 4,621,077, is a specific inhibitor of osteoclast-mediated bone resorption and is indicated for the treatment of urolithiasis and inhibiting bone reabsorption.

Alendronate is commercially available as alendronate sodium trihydrate in the form of tablets and oral solution under the trade name Fosamax® (Merck). Tablets have certain disadvantage for patients who are unable to swallow tablets readily. To overcome the problem of difficulty in swallowing, alendronate in solution formulation have been developed with an increased patient compliance. Commercially available alendronate oral solution contain 91.35 mg of alendronate monosodium salt trihydrate, which is molar equivalent to 70 mg of free acid alendronate as active ingredient and excipients such as sodium citrate dihydrate and citric acid anhydrous as buffering agents, sodium propylparaben 0.0225% and sodium butylparaben 0.0075% as preservatives, sodium saccharin, artificial raspberry flavor and purified water.

Given below are the patents/patent publications, which disclose aqueous oral formulations of alendronate.

U.S. Pat. No. 4,814,326 discloses aqueous solution of diphosphonic acid with amino carboxylic acid as stabilizer with pH 4.5-5.65.

U.S. Pat. No. 5,462,932 discloses composition comprising a pharmaceutically effective amount of alendronate, in a pharmaceutically acceptable carrier and a sufficient amount of a buffer to maintain a pH of the composition in the range of 2 to 8 and complexing agent to prevent the precipitation of alendronate sodium in aqueous solution.

U.S. Pat. No. 5,994,329 discloses liquid composition comprising alendronate monosodium trihydrate, sodium propylparaben, sodium butylparaben, sodium citrate dihydrate, citric acid anhydrous, sodium saccharin, sodium hydroxide and water.

US 2003/0139378 discloses an oral liquid composition comprising: a) a therapeutically effective amount of at least one bisphosphonate or a pharmaceutically acceptable salt thereof, b) a pharmaceutically acceptable carrier, and c) a pharmaceutically acceptable buffer, wherein a dose of said oral liquid pharmaceutical composition has a buffering capacity sufficient to buffer at least 50 mL of 0.1 N HCl to a pH of greater than or equal to 3.5.

US 2004/087550 discloses a composition for prevention of metabolic diseases of bones comprising: at least one bisphosphonate including alendronate sodium, viscosity agents comprising carboxymethylcellulose and xanthan gum; at least one flavoring agent and purified water.

WO 98/14196 discloses an aqueous liquid formulation comprising: alendronic acid; a sufficient amount of a buffer such that the pH of the formulation is between approximately 3.5 and approximately 7.5 and 15 ml of the formulation is able to raise the pH of 50 ml 0.1N HCl to a pH of at least 3 and optionally, one or more additional agents selected from the group consisting of preservatives, flavoring agents, colorants, and sweeteners.

WO 08/028547 discloses liquid composition for prevention of bone metabolic diseases, comprising alendronic acid or its acceptable pharmaceutical salts, or mixtures thereof, a viscosity agent selected from the group consisting of alginate, propylglycolalginate, arabic gum (acacia), xanthan gum, guar gum, locust bean, carrageenan gum, karaya gum, tragacanth gum, chitosan, sodium carboxymethyl cellulose and carbomer or mixtures thereof, at least one flavoring agent and purified water.

The above prior art references discloses various liquid formulations of alendronate sodium using amino carboxylic acid, buffer, viscosity agents and complexing agent to stabilize alendronate in aqueous formulations.

However, still there is a need to develop stable aqueous formulation comprising alendronate wherein said formulation is free of buffers and stabilizers. The inventors of the present invention surprisingly found that stable alendronate solution can be prepared by maintaining pH less than 5.0 using inorganic acid without using any buffers and stabilizers.

OBJECTIVE OF THE INVENTION

Accordingly, the main objective of the present invention is to provide stable aqueous formulation comprising alendronate sodium.

Yet another objective of the present invention is to provide stable aqueous formulation comprising alendronate sodium in such a way that it will comply with the reference product.

Yet another objective of the present invention is to provide simple process for the preparation of stable aqueous formulation of alendronate sodium.

SUMMARY OF THE INVENTION

Accordingly, the main embodiment of the present invention is to provide stable aqueous oral formulation comprising alendronate sodium and inorganic acid, wherein the said formulation has pH in the range of about 2 to 5 and is essentially free of buffers and stabilizers.

DETAILED DESCRIPTION OF THE INVENTION

Yet in another embodiment of the present invention, the stable aqueous formulation further comprises one or more excipients selected from preservatives, sweetening agents and flavoring agents.

The inorganic acid according to the present invention includes dilute hydrochloric acid, dilute sulfuric acid, dilute phosphoric acid and the like. The inorganic acid used in the formulation inhibits the microbial growth and makes the solution stable for a prolonged period of time.

Suitable preservatives used according to the present invention are selected from sodium benzoate, potassium sorbate, benzyl alcohol, parabens (p-hydroxybenzoic acids esters)

such as methylparaben, ethylparaben, propylparaben, butylparaben and the like or mixtures thereof. The amount of preservatives used may be in the range of about 0.02 to about 2% by weight of the composition.

Suitable sweetening agents include saccharin sodium, sodium cyclamate, sorbitol, xylitol, sucrose, glycerol, aspartame and the like. The amount of sweetening agent used may be in the range of about 0.1 to about 2% by weight of the composition.

Suitable flavoring agents include peppermint flavor, spearmint flavor, lime flavor, apple flavor, pear flavor, peach flavor, raspberry flavor, plum flavor, pineapple flavor and the like. The amount of flavorants used may be in the range of about 0.05 to about 5% by weight of the composition.

In another embodiment, the amount of alendronate sodium used according to the present invention is in the range of about 1% to about 30% by weight of the composition.

In a preferred embodiment, the stable aqueous oral formulation comprises about 1% to about 30% by weight of alendronate sodium, an inorganic acid such as dilute hydrochloric acid, dilute sulfuric acid and dilute phosphoric acid; about 0.02 to about 2% by weight of preservatives such as methylparaben, ethylparaben, propylparaben and butylparaben; about 0.1 to about 2% by weight of sweetening agents such as saccharin sodium, sodium cyclamate, sorbitol, xylitol; about 0.05 to about 5% by weight of flavoring agents such as peppermint flavor, spearmint flavor and artificial raspberry flavor, wherein the said formulation has pH in the range of about 2 to 5 and is essentially free of buffers and stabilizers.

In a preferred embodiment, the stable aqueous oral formulation comprises

| | |
|---|---|
| alendronate sodium | 50 to 100 mg |
| inorganic acid | 0.0001 to 0.001 mg |
| preservatives | 30 to 80 mg |
| sweetening agents | 20 to 200 mg |
| flavoring agents | 20 to 100 mg |
| purified water | QS to 75 ml, | wherein the said formulation has pH in the range of about 2 to 5 and is essentially free of buffers and stabilizers.

In another embodiment of the present invention, there is provided a process for the preparation of stable aqueous formulation comprising alendronate sodium and inorganic acid, wherein the said formulation has pH in the range of about 2 to 5 and is essentially free of buffers and stabilizers, comprises the steps of:

i) dissolving the preservatives in water,
ii) adding sweetening agent to the solution of step (i),
iii) adding alendronate sodium to the solution of step (ii) and stirring it to get clear solution,
iv) adding inorganic acid to the solution of step (iii),
v) adjusting the pH of solution using 0.85% v/v hydrochloric acid,
vi) adding flavoring agent to the solution of step (v) and
vii) finally making up the volume with water to obtain a clear solution.

The stable aqueous formulation of alendronate sodium of the present invention are useful in the therapeutic or prophylactic treatment of disorders in calcium and phosphate metabolism and associated diseases such as osteoporosis which includes post-menopausal osteoporosis, steroid-induced osteoporosis, male osteoporosis, disease-induced osteoporosis, idiopathic osteoporosis, Paget's disorder, abnormally increased bone turnover, periodontal disease, localized bone loss associated with periprosthetic osteolysis and bone fractures.

The following examples further exemplify the invention and are not intended to limit the scope of the invention. It is obvious to those skilled in the art to find out the composition for other dosage forms and substitute the equivalent excipients as described in this specification or with the one known to the industry.

EXAMPLE 1

| Ingredients | Mg/75 ml |
|---|---|
| Alendronate sodium | 91.363 |
| Saccharin sodium | 75.000 |
| Propylparaben sodium | 16.875 |
| Butylparaben sodium | 5.625 |
| Artificial raspberry flavor | 50.000 |
| Hydrochloric acid | 0.000765 |
| Hydrochloric acid | QS for pH adjustment |
| Purified water | QS to 75.000 ml |

The processing steps involved in manufacturing a stable aqueous solution given in example 1 are given below:

1. propylparaben sodium and butylparaben sodium were dissolved in water under continuous stirring,
2. to the solution of step (1) saccharin sodium was added and stirred to obtain clear solution,
3. to the solution of step (2) alendronate sodium was added and again stirred to obtain clear solution,
4. hydrochloric acid was added to the solution of step (3),
5. pH of the solution was adjusted using 0.85% v/v hydrochloric acid,
6. artificial raspberry flavor was added to the solution obtained in step (5) and
7. finally the volume was adjusted with water.

The formulations given in examples 2 and 3 were prepared using similar procedure described in example 1.

EXAMPLE 2

| Ingredients | Mg/75 ml |
|---|---|
| Alendronate sodium | 91.363 |
| Saccharin sodium | 75.000 |
| Propylparaben sodium | 16.875 |
| Artificial raspberry flavor | 50.000 |
| Hydrochloric acid | 0.000765 |
| Hydrochloric acid | QS for pH adjustment |
| Purified water | QS to 75.000 ml |

EXAMPLE 3

| Ingredients | Mg/75 ml |
|---|---|
| Alendronate sodium | 91.363 |
| Saccharin sodium | 75.000 |
| Propylparaben sodium | 16.875 |
| Methylparaben sodium | 33.750 |

-continued

| Ingredients | Mg/75 ml |
|---|---|
| Artificial raspberry flavor | 50.000 |
| Hydrochloric acid | 0.000765 |
| Hydrochloric acid | QS for pH adjustment |
| Purified water | QS to 75.000 ml |

Stability Data

Aqueous alendronate sodium solutions prepared according the present invention were found to be stable. The amount of alendronate sodium was analyzed for 1 month at 40° C. and 75% relative humidity. The stability data is given in table 1.

TABLE 1

| | % of Alendronate sodium | |
|---|---|---|
| Example No. | Initial | 1M |
| 1 | 101.6 | 101 |
| 2 | 102.1 | 103.1 |
| 3 | 99.3 | 99.9 |

We claim:

1. A stable aqueous oral formulation comprising alendronate sodium and inorganic acid, wherein the said formulation has pH in the range of about 2 to 5 and is essentially free of buffers and stabilizers.

2. The aqueous formulation as claimed in claim 1, wherein the inorganic acid is selected frrm dilute hydrochloric acid, dilute sulfuric acid and dilute phosphoric acid.

3. The aqueous formulation as claimed in claim 1, further comprise one or more excipients such as preservatives, sweetening agents and flavoring agents.

4. The aqueous formulation as claimed in claim 3, wherein the preservative is selected from sodium benzoate, potassium sorbate, benzyl alcohol, methylparaben, ethylparaben, propylparaben and butylparaben or a combination thereof.

5. The aqueous formulation as claimed in claim 3, wherein the sweetening agent is selected from saccharin sodium, sodium cyclamate, sorbitol, xylitol, sucrose, glycerol and aspartame or a combination thereof.

6. The aqueous formulation as claimed in claim 3, wherein the flavoring agent is selected from peppermint flavor, spearmint flavor, lime flavor, apple flavor, pear flavor, peach flavor, raspberry flavor, plum flavor and pineapple flavor or a combination thereof.

7. A stable aqueous oral formulation comprising about 1% to about 30% by weight of alendronate sodium, an inorganic acid such as dilute hydrochloric acid, dilute sulfuric acid and dilute phosphoric acid; about 0.02 to about 2% by weight of preservatives such as methylparaben, ethylparaben, propylparaben and butylparaben; about 0.1 to about 2% by weight of sweetening agents such as saccharin sodium, sodium cyclamate, sorbitol, xylitol; about 0.05 to about 5% by weight of flavoring agents such as peppermint flavor, spearmint flavor and artificial raspberry flavor, wherein the said formulation has pH in the range of about 2 to 5 and is essentially free of buffers and stabilizers.

8. A stable aqueous oral formulation comprising

| alendronate sodium | 50 to 100 mg |
|---|---|
| inorganic acid | 0.0001 to 0.001 mg |
| preservatives | 30 to 80 mg |
| sweetening agents | 20 to 200 mg |
| flavoring agents | 20 to 100 mg |
| purified water | QS to 75 ml, | wherein the said formulation has pH in the range of about 2 to 5 and is essentially free of buffers and stabilizers.

9. A process for preparing stable aqueous oral formulation comprising alendronate sodium and inorganic acid, wherein the said formulation has pH in the range of about 2 to 5 and is essentially free of buffers and stabilizers, which comprises the steps of:
  i) dissolving the preservatives in water,
  ii) adding sweetening agent to the solution of step (i),
  iii) adding alendronate sodium to the solution of step (ii),
  iv) adding hydrochloric acid to the solution of step (iii),
  v) adjusting the pH of solution using 0.85% v/v hydrochloric acid,
  vi) adding flavoring agent to the solution of step (v) and
  vii) finally making up the volume with water to obtain a clear solution.

10. A method of treating osteoporosis by administering the stable aqueous formulation of alendronate sodium as claimed in claim 1.

* * * * *